United States Patent [19]

Parekh et al.

[11] Patent Number: 4,959,197

[45] Date of Patent: Sep. 25, 1990

[54] FILTER CANISTER FOR IMMUNOASSAYS

[75] Inventors: Bharat S. Parekh, Pleasant Hill; William F. Link, Richmond; Stephen R. Coates, Orinda; George B. LaMotte III, Lakespur, all of Calif.

[73] Assignee: Bio-Rad Laboratories, Inc., Hercules, Calif.

[21] Appl. No.: 241,444

[22] Filed: Sep. 7, 1988

[51] Int. Cl.[5] ........................ B01L 11/00; B01L 3/00; C12M 1/16; C12M 1/20

[52] U.S. Cl. .................................... 422/101; 422/102; 435/299; 435/301

[58] Field of Search ................ 422/101, 102; 435/299, 435/301

[56] References Cited

U.S. PATENT DOCUMENTS

| | | | |
|---|---|---|---|
| 3,888,629 | 6/1975 | Bagshawe | 23/230 B |
| 4,632,901 | 12/1986 | Valkirs et al. | 435/5 |
| 4,693,834 | 9/1987 | Hossom | 210/767 |
| 4,797,259 | 1/1989 | Matkovich et al. | 422/101 |
| 4,797,260 | 1/1989 | Parker | 422/101 |

FOREIGN PATENT DOCUMENTS

| | | |
|---|---|---|
| 0217403 | 8/1987 | European Pat. Off. . |
| 8505451 | 12/1985 | PCT Int'l Appl. . |

*Primary Examiner*—Christine Nucker
*Assistant Examiner*—Karen I. Kruper
*Attorney, Agent, or Firm*—Townsend and Townsend

[57] ABSTRACT

A canister for holding a solid phase support for use in a biospecific binding assay is disclosed. The canister consists of a receptacle and cap, both shaped to mate with each other in a snug fit, the cap having a central opening spanned by the solid phase in the form of a thin porous disk. The central opening is surrounded by a raised surface which forms a protective wall avoiding inadvertent contact of the disk by the user or surrounding objects. The cap and receptacle are constructed so as to provide a vent when the parts are joined, providing gravitational flow of a test sample across the porous disk into the interior of the receptacle.

5 Claims, 2 Drawing Sheets

FILTER CANISTER FOR IMMUNOASSAYS

This invention relates to immunoassays involving the use of solid materials for the immobilization of binding members. In particular, this invention relates to flow-through mounting arrangements for filters or porous membranes.

BACKGROUND AND SUMMARY OF THE INVENTION

Many types of immunoassays involve the interaction of a liquid sample with a solid material, and a determination of whether or not a reaction has taken place between species in the sample and species immobilized on the solid surface. The immobilization may be achieved either by covalent chemical bond or nonspecific binding such as electrostatic attraction, hydrophobic interaction or hydrogen bonding.

Handling of the solid phase by the operator is frequently a delicate procedure. In some cases, the membrane is thin and fragile. The membrane can be contaminated by inadvertent touching to the extent that its accuracy and reproducibility may be impaired. In addition, the species immobilized on the membrane may contain infectious material raising a safety hazard to those handling the membrane.

Drawing liquid through the solid phase is also problematic in some cases. Absorbent pads have been used on the downstream side of the membrane, but this requires very close contact between the membrane and the absorbent pad. Otherwise, bubbles form which obstruct the flow.

The present invention provides a canister for the support of a flow-through solid phase, which protects the solid phase and any species immobilized on it from inadvertent contact by the operator or other equipment, and permits flow across the solid phase solely by the force of gravity, retaining all liquids for proper disposal. The canister is comprised of two parts, an open-top receptacle and a cap for the receptacle, the cap designed to support the solid phase material. The cap has a central opening surrounded by a raised surface. The solid phase material spans the opening, and the raised surface serves as a protective wall encircling the material. The cap and receptacle are shaped to fit snugly and securely together and yet leave a gap to vent the interior of the receptacle to the atmosphere.

Further features and advantages of the invention will become evident from the following description.

DETAILED DESCRIPTION OF THE INVENTION AND PREFERRED EMBODIMENTS

Figure 1:
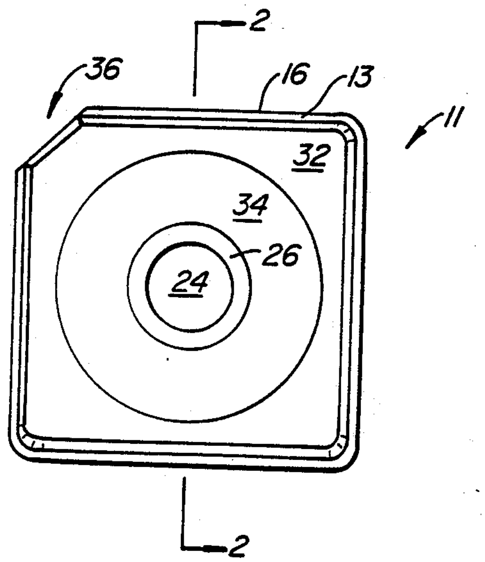
FIG. 1 is a top view of the cap portion of a canister in accordance with an illustrative embodiment of the invention.
Figure 3:
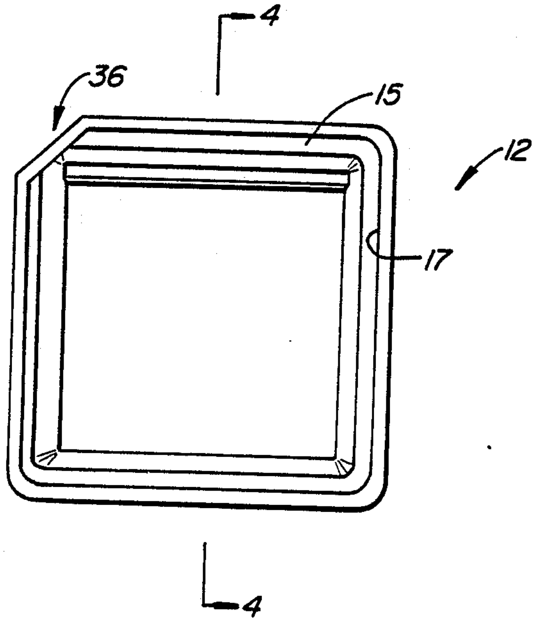
FIG. 3 is a top view of a receptacle portion of a canister designed to mate with the cap portion of FIG. 1.

FIG. 1 depicts the cap 11 or upper portion of the canister. The cap holds the thin porous material which serves as the solid support. The receptacle 12 or lower portion of the canister is shown in FIG. 3. The two are designed to fit together in a snug fashion, i.e., to retain one another until pulled apart. This snug fit is achieved by a laterally protruding rib 13 which encircles the cap, except for the cutoff corner at the upper left side in the drawing. The lower face 14 of this rib 13 rests on a ledge 15 along the internal wall of the receptacle 12, while the outer edge 16 of the rib contacts the inner wall 17 of an expanded portion 18 of the receptacle 12 above the ledge 15. As mentioned above, the fit is sufficiently snug to hold the parts together once assembled, yet permit their easy separation by the operator pulling them apart. Alternatively, the parts can be glued together if necessary for a particular assay.

Figure 2:
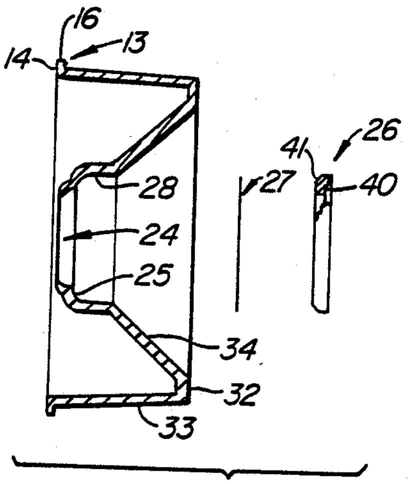
FIG. 2 is a side elevation of the cap portion of FIG. 1 in cutaway, taken along the line 2—2 of FIG. 1, and exploded to show the solid phase material and retaining ring.

The cap has central opening 24 across which the solid phase is placed, permitting flow through the cap into the receptacle. In this embodiment, the solid phase is retained across the opening by a ledge 25 surrounding the opening, and a ring 26 which fits over the ledge 25. The solid support is represented in FIG. 2 by element 27. Vertical walls 28 surrounding the central opening 24 define a straight passage for insertion of the ring 26 and holding it in place. The ring is of a resilient material which fits snugly within this passage.

Surrounding the central opening 24 is a raised surface 32 effectively forming a protective wall 33 guarding the solid support against inadvertent contact. The inner surfaces 34 of this protective wall are sloping inward toward the center to form a conical-shaped surface to direct fluids toward the solid support stretched across the central opening 24.

As mentioned above, the cap 11 and receptacle 12 are designed to fit together in such a manner that while snug, they leave an opening which serves to communicate the interior 35 of the receptacle with the atmosphere as a means of venting the canister as liquids are entering it through the porous solid phase spanning the central opening 24. In the embodiment shown in the drawings, this gap is formed at an angled cutoff corner 36 represented by the upper right corner in FIGS. 1 and 3. The rib 13 running along the periphery of the cap 11 terminates at each end of this angled corner 36. Likewise, the inner ledge 15 along the inner wall of the receptacle terminates as well at this angled corner 36.

Figure 5:
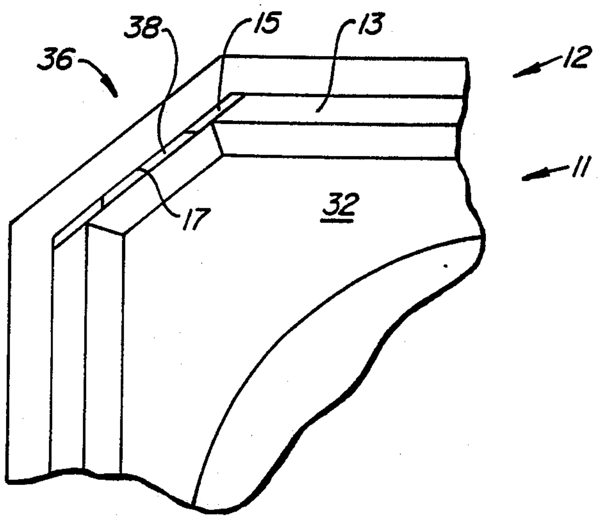
FIG. 5 is an enlarged detail view of one corner of the two portions of the canister shown in FIGS. 1–4, assembled together. The corner shown is that corresponding to the upper left corner as shown in FIGS. 1 and 3.

FIG. 5 shows the receptacle 12 with the cap 11 in place. At the angled corner 36 the outer sloping wall 37 of the cap 11 does not meet the inner wall 17 of the receptacle, and thereby leaves a gap 38 between the two. This gap 38 forms an open passage for venting as described above.

Returning to FIG. 2, the ring 26 is shown in partially cutaway to indicate sloping surfaces 40, 41. The upper sloping surface 40 aids in directing all fluid toward the solid support.

Figure 4:
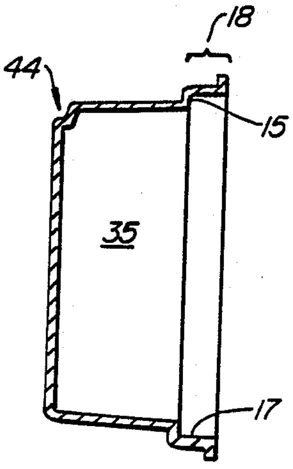
FIG. 4 is a side elevation of the receptacle portion of FIG. 3, taken along line 4—4 of FIG. 3, shown in cutaway.

The overall shape of the canister in this particular embodiment is designed to encourage mating of the canister with other pieces of apparatus to assure proper orientation. The angled corner 36 is one feature serving this purpose. Another feature is a registration groove 44 (FIG. 4) along one lower edge of the receptacle.

The canister shown in these figures, as well as other structures within the scope of the invention, are designed to support solid phases of a wide range of materials. These include such materials as glass fibers and nitrocellulose and any other thin porous material or membrane including all such materials conventionally used in biospecific binding assays. The solid phase may be used as a simple filter, or as a support to which a binding member is bound. Such binding members may be antibodies, antigens, or other known types of species. In use, the cap and receptacle are joined with the solid phase secured in place, and the test sample is added to the cap above the solid phase. The sample then drains through the solid phase by gravitational force, during which time species in the sample which react either with the solid phase or with the binding member previously secured to the solid phase become thus immobilized on the solid phase. Excess sample may then be washed away, and subsequent procedures are carried out in accordance with the particular type of assay being done. For example, an antibody-enzyme conjugate may be added, and excess reagent then washed away, followed by addition of an enzyme substrate, permitting color to develop on the surface of the solid phase.

The foregoing is offered primarily for purposes of illustration. It will be readily apparent to those skilled in the art that other materials, shapes, structures and procedures beyond those described above may be utilized without departing from the spirit and scope of the invention.

What is claimed is:

1. A canister for holding a fluid-permeable membrane for use in a biospecific binding assay, comprising:

a cup-shaped receptacle closed at the bottom and sides and open at the top;

a fluid-permeable membrane;

a cap shaped to mate with said receptacle, said cap having a central opening sized to receive said fluid-permeable membrane and surrounded by a raised surface;

removable means for securing said fluid-permeable membrane to said cap across said opening; and means for venting the interior of said receptacle to the atmosphere when said cap and said receptacle are joined.

2. A canister in accordance with claim 1 in which said central opening and said raised surface are joined by a sloping surface.

3. A canister in accordance with claim 1 in which said securing means comprises a ledge surrounding said central opening along the interior thereof and means for affixing the periphery of said fluid-permeable membrane to said ledge.

4. A canister in accordance with claim 3 in which said affixing means comprises a resilient ring sized to fit snugly in the interior of said central opening over said ledge.

5. A canister in accordance with claim 1 in which said venting means is comprised of means defining a gap between said receptacle and said cap when said receptacle and said cap are joined.

* * * * *